US009332751B2

(12) United States Patent
Unal et al.

(10) Patent No.: US 9,332,751 B2
(45) Date of Patent: May 10, 2016

(54) FOOD PACKAGING MATERIAL WITH ANTIBACTERIAL, ETHYLENE SCAVENGING AND BARRIER PROPERTIES

(71) Applicant: Sabanci Universitesi, Istanbul (TR)

(72) Inventors: Hayriye Unal, Istanbul (TR); Serkan Unal, Istanbul (TR); Yusuf Ziya Menceloglu, Istanbul (TR); Fevzi Cakmak Cebeci, Istanbul (TR)

(73) Assignee: SABANCI UNIVERSITESI, Istanbul (TR)

( * ) Notice: Subject to any disclaimer, the term of this patent is extended or adjusted under 35 U.S.C. 154(b) by 0 days.

(21) Appl. No.: 14/795,301

(22) Filed: Jul. 9, 2015

(65) Prior Publication Data

US 2016/0007591 A1 Jan. 14, 2016

(30) Foreign Application Priority Data

Jul. 9, 2014 (EP) .................................. 14176379

(51) Int. Cl.
| | |
|---|---|
| *A01N 25/10* | (2006.01) |
| *A01N 65/22* | (2009.01) |
| *A01N 25/34* | (2006.01) |
| *A01N 25/04* | (2006.01) |
| *B65D 65/38* | (2006.01) |
| *B65D 81/28* | (2006.01) |
| *B05D 1/00* | (2006.01) |

(52) U.S. Cl.
CPC ................ *A01N 25/10* (2013.01); *A01N 25/04* (2013.01); *A01N 25/34* (2013.01); *A01N 65/22* (2013.01); *B05D 1/007* (2013.01); *B65D 65/38* (2013.01); *B65D 81/28* (2013.01)

(58) Field of Classification Search
CPC ....... A01N 25/10; A01N 65/22; A01N 25/34; A01N 25/04; B65D 65/38; B65D 81/28; B05D 1/007
See application file for complete search history.

(56) References Cited

U.S. PATENT DOCUMENTS

2007/0106006 A1    5/2007    Cooper et al.

FOREIGN PATENT DOCUMENTS

| CN | 1746216 A | 3/2006 |
| EP | 0515764 A2 | 12/1992 |
| WO | 2005/000369 A1 | 1/2005 |

OTHER PUBLICATIONS

Abdullayev et al, Halloysite clay nanotubes as a ceramic "skeleton" for functional biopolymer composites with sustained drug release, Apr. 2013, Journal of Materials Chemistry B, 1, pp. 2894-2903.*
Harrington, Cinnamon and oregano show antimicrobial prowess in active packaging, Aug. 2010, FoodProductionDaily.com, pp. 1-2. http://www.foodproductiondaily.com/content/view/print/318356.*
Arora et al., "Antimicrobial activity of spices", International Journal of Antimicrobial Agents, 12: 257-262 (1999).

(Continued)

*Primary Examiner* — Trevor Love
(74) *Attorney, Agent, or Firm* — Nixon Peabody LLP; Leena H. Karttunen Contarino

(57) ABSTRACT

The present invention provides novel use of the polymeric films comprising halloysite nanotubes as a packaging material for food products. Said halloysite nanotubes are incorporated with active agents such as antibacterial agents preferably of natural type for providing antibacterial, barrier and ethylene scavenging properties.

6 Claims, 3 Drawing Sheets

(56) References Cited

OTHER PUBLICATIONS

Duncan, "Applications of nanotechnology in food packaging and food safety: Barrier materials, antimicrobials and sensors", Journal of Colloid and Interface Science, 363: 1-24, (2011);.
Friedman et al., "Bactericidal Activities of Plant Essential Oils and Some of Their Isolated Constituents against Campylobacter jejuni, *Escherichia coli*, Listeria monocytogenes, and *Salmonella enterica*", Journal of Food Protection, 55(10): 1545-1560 (2002).
Gopakumar et al., "Influence of clay exfoliation on the physical properties of montmorillonite/polyethylene composites", Polymer, 43(20): 5483-5491 (2002).
Hambir et al., "PP/clay nanocomposites: A study of crystallization and dynamic mechanical behavior", Journal of Polymer Science Part B: Polymer Physics, 39(4): 446-450 (2001).
Lee et al., "Antimicrobial packaging of raw beef, pork and turkey using silver-zeolite incorporated into the material", International Journal of Food Science & Technology, 46(11): 2382-2386 (2011).
Martínez-Abad et al., "Evaluation of silver-infused polylactide films for inactivation of *Salmonella* and feline calicivirus in vitro and on fresh-cut vegetables", International Journal of Food Microbiology, 162(1): 89-9 (2013).
Mauriello et al., "Development of polythene films for food packaging activated with an antilisterial bacteriocin from Lactobacillus curvatus 32Y", Journal of Applied Microbiology, 97: 314-322, (2004).
Periago et al., "Use of Carvacrol and Cymene to Control Growth and Viability of Listeria monocytogenes Cells and Predictions of Survivors Using Frequency Distribution Functions", Journal of Food Protection, 67: 1408-1416 (2004).
Scaffaro et al., "Incorporation of Nisin in Poly (Ethylene-Co-Vinyl Acetate) Films by Melt Processing: A Study on the Antimicrobial Properties", Journal of Food Protection, 7: 1137-1143 (2011).
Weng et al., "Antimicrobial Food Packaging Materials from Poly-(ethylene-co-methacrylic acid)", LWT—Food Science and Technology, 32: 191-195 (1999).
Yossa et al., "Antibacterial Activity of Cinnamaldehyde and Sporan against *Escherichia coli* O157:H7 and *Salmonella*", Journal of Food Processing and Preservation (2012).

\* cited by examiner

FOOD PACKAGING MATERIAL WITH ANTIBACTERIAL, ETHYLENE SCAVENGING AND BARRIER PROPERTIES

CROSS-REFERENCE TO RELATED APPLICATION

This application claims priority under 35 U.S.C. §119(a) to EP Application No. 14176379.7 filed Jul. 9, 2014, the contents of which are incorporated herein by reference in its entirety.

TECHNICAL FIELD OF THE INVENTION

The present invention relates to modified polymeric packaging materials having antibacterial, ethylene scavenging and barrier properties, and more particularly the invention pertains to polymeric packaging materials containing halloysite nanotubes with multifunctional properties.

BACKGROUND OF THE INVENTION

Active and multifunctional packaging materials are facing increasing demand because of the changing trend of the customer needs such as safety and long shelf life of the food material without however interfering with processed materials, preservatives and additives. Contrary to conventional food packaging that is inert to the food; active food packaging has the ability to act against the contaminants and to remove them. Active packaging functions like being antibacterial, ability to scavenge spoiling molecules, and impermeability to gases are achieved by the integration of active components into the food packaging materials. In order to have safe active food packaging, it is crucial to choose active packaging components that do not pose any risks to human health.

In prior art, antibacterial properties are imparted to the food packaging material through incorporation of antibacterial agents including organic acids, bacteriocins, and silver ions. These agents were proven to result in packaging material that can act against food pathogens (WENG Y.-M., Chen M.-J., Chen W., Antimicrobial Food Packaging Materials from Poly (ethylene-co-methacrylic acid), LWT—Food Science and Technology, 32, 191-195, (1999); MAURIELLO G., Ercolini D., La Storia A., Casaburi A., Villani F., Development of polythene films for food packaging activated with an antilisterial bacteriocin from Lactobacillus curvatus 32Y, Journal of Applied Microbiology, 97, 314-322, (2004); SCAFFARO R., Botta L., Marineo S., Puglia A. M., Incorporation of Nisin in Poly (Ethylene-Co-Vinyl Acetate) Films by Melt Processing: A Study on the Antimicrobial Properties, Journal of Food Protection® 74, 1137-1143, (2011); LEE J., Lee Y.-H., Jones K., Sharek E., Pascall M. A., Antimicrobial packaging of raw beef, pork and turkey using silver-zeolite incorporated into the material, International Journal of Food Science & Technology, 46, 2382-2386, (2011); MARTÍNEZ-ABAD A., Ocio M. J., Lagar& J. M., Sanchez G., Evaluation of silver-infused polylactide films for inactivation of *Salmonella* and feline calicivirus in vitro and on fresh-cut vegetables, International Journal of Food Microbiology, 162, 89-94, (2013)).

There are provided safer and more natural alternatives of antimicrobial agents, namely essential oils which are volatile components of herbs and spices, and many of them and their active components have been proven to have antibacterial activity against food pathogens. Among these, thyme oil and cinnamon oil are particularly preferred as they have the well established antimicrobial activities against different bacteria because they include carvacrol and cinnamaldehyde, respectively, as the major components (FRIEDMAN M., Henika P. R., Mandrell R. E., Bactericidal Activities of Plant Essential Oils and Some of Their Isolated Constituents against *Campylobacter jejuni, Escherichia coli, Listeria monocytogenes*, and *Salmonella enterica*, Journal of Food Protection, 65, 1545-1560, (2002); ARORA D. S., Kaur J., Antimicrobial activity of spices, International Journal of Antimicrobial Agents, 12, 257-262, (1999)). Further, Paula et al. reports that carvacrol from thyme oil and cymene from cinnamon oil synergistically improve controlling of the growth and viability of *Listeria monocytogenes* cells (PAULA M. P., Bego, Ntilde, A D., Pablo S. F., Aacute, Ndez, Alfredo P., Use of Carvacrol and Cymene To Control Growth and Viability of *Listeria monocytogenes* Cells and Predictions of Survivors Using Frequency Distribution Functions, Journal of Food Protection, 67, 1408-1416, (2004)). In another assay, Yossa et al. reports that cinnamaldehyde of the cinnamon oil eliminates completely the *E. coli* and *Salmonella* cells (YOSSA N., Patel J., Macarisin D., Millner P., Murphy C., Bauchan G., Lo Y. M., Antibacterial Activity of Cinnamaldehyde and Sporan against *Escherichia coli* O157:H7 and *Salmonella*, Journal of Food Processing and Preservation, nia-n/a, (2012)). Essential oils have been incorporated into the polymeric films as a way of developing safe antibacterial food packaging material. While this approach results in some antibacterial activity, the effectiveness is very low compared to the activity of free essential oils. A system that enables controlled loading/release of essential oils into/from the polymeric films that enhances the antibacterial activity of the food packaging material is needed.

There are various methods and products in the art, for preserving food material from negative effects of ethylene gas. Fruits and vegetables, for instance secrete ethylene as a phytohormone, and this accelerates the ripening and consequently rotting and deterioration of the food material which is undesirable. A method to introduce ethylene scavenging properties for instance involves using of potassium permanganate as an ethylene oxidizing agent as disclosed in WO 2005/000369 A1 and EP 0 515 764 A2. Potassium permanganate is incorporated into absorbent materials having high surface area such as alumina, silica, clay and activated carbon. However potassium permanganate is prohibited in Europe and limited latitude exists in the U.S. as far as the absorbent material is stored in sacs because of the toxicity of potassium permanganate. Incorporating different minerals into polymeric films, on the other hand is also well known and such products are already available in the market (e.g. Peakfresh®, Australia; Greenbags, U.S.A.; Magiclivefresh, Turkey).

Food packaging materials with barrier properties against atmospheric gases, water vapor and volatile compounds are required. Synthetic polyolefins which have excellent thermal and mechanical properties are disadvantegous as food packaging materials due to their permeability to gases. While the use of multilayered polymeric films ensures barrier properties, their high cost and problems associated with recycling these films limit their commercial use. Therefore, in prior art, alternative materials to be incorporated within polyolefins for ensuring the aforesaid properties in packaging materials have been focus of the researchers. Nanoclay particles, mainly montmorillonite have been applied as fillings in nanocomposites as barrier components against gas molecules (DUNCAN T. V., Applications of nanotechnology in food packaging and food safety: Barrier materials, antimicrobials and sensors, Journal of Colloid and Interface Science, 363, 1-24, (2011); GOPAKUMAR T. G., Lee J. A., Kontopoulou M., Parent J. S., Influence of clay exfoliation on the physical properties of montmorillonite/polyethylene composites, Polymer, 43, 5483-5491, (2002); HAMBIR S., Bulakh N., Kodgire P., Kalgaonkar R., Jog J. P., PP/clay nanocomposites: A study of crystallization and dynamic mechanical behavior, Journal of Polymer Science Part B: Polymer Physics, 39, 446-450, (2001)). Barrier properties can be achieved if effective adhesion between the fillings and the polymer occurs, which is however hardly achievable. Montmorillonite exhibits good compatibility with polymers having higher surface energy such as polyamides, albeit is problemmatic with polymers of having lower surface energy such as polyethylene (PE) and polypropylene (PP) because of the lower adhesion of such polymers that causes the nanoclay molecules be hardly dispersible in the polymer blend.

Therefore, there exists continuing need for a modified film packaging that can have antimicrobial, gas scavenging and barrier properties while having also easy applicability to conventional olefins, particularly thermoplastics and more particularly to plastics of having lower surface energy such as PE and PP.

Nanocomposite materials including halloysite nanotubes incorporated into polymeric moieties such as thermoplastic polymers are disclosed, for instance in CN 1746216 A and US 2007106006 A1, whereas the said composite materials are proposed for different application areas such as coatings for fire retarding, anti-corrosion and self-cleaning of surfaces as well as plastics of different functionalities. However, there appears no study within state of the art as to the use of such nanocomposites in the form of plastic films as a food packaging material. The present invention eliminates the problems faced in the prior art by way of using the packaging materials incorporated with halloysite nanotubes which are found as efficient materials to provide good antibacterial, barrier and scavenging properties in the specific area of food products by simple production and modification procedures.

It is therefore an objective of the present invention to provide a food packaging material in the form of polymeric films or a coating for polymeric films having good antibacterial, barrier and scavenging properties.

A further object of the present invention is to provide antibacterial properties without using agents detrimental or harmful to human health.

Another object of the present invention is to provide packaging materials having satisfactory barrier and scavenging properties while being easily recyclable.

Still a further object of the present invention is to provide modified polymeric films for food packaging providing all of antibacterial, barrier and scavenging properties within the same product by specific arrangements and modifications.

Further objects and aspects of the current invention shall be apparent for those skilled in the art in view of the following statements and description, and these objectives are presently solved by novel products and specific uses thereof as disclosed in the appended claims.

DETAILED DESCRIPTION OF THE INVENTION

Figure 1:
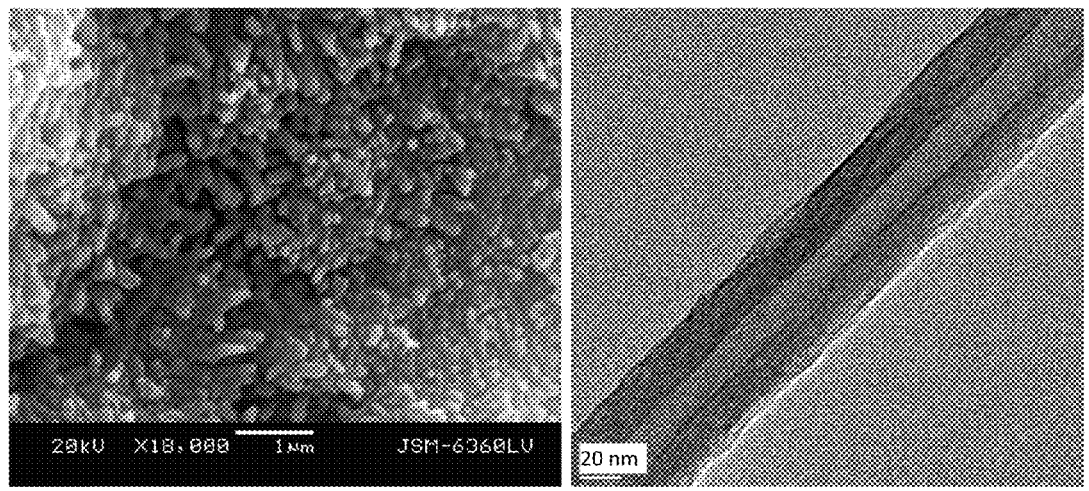
FIG. 1 shows SEM micrographs of the halloysite nanotubes of the present invention.

The proposed invention relates to a packaging material in the form of a polymeric film incorporated with halloysite nanotubes (HNT) to provide antibacterial, ethylene scavenging, and barrier properties. The present invention further relates to specific use of such a polymeric film as a food packaging material as well as modified forms of said polymeric materials for providing improved features in terms of the desired properties mentioned above. HNTs per se, containing aluminum, silicon and hydrogen as the major components are well known in the art, and are commercially available in the market (Eczacibasi ESAN, Turkey). As shown in FIG. 1, HNTs exhibit hollow tubular structures that are suitable to store certain materials therein.

Figure 2:
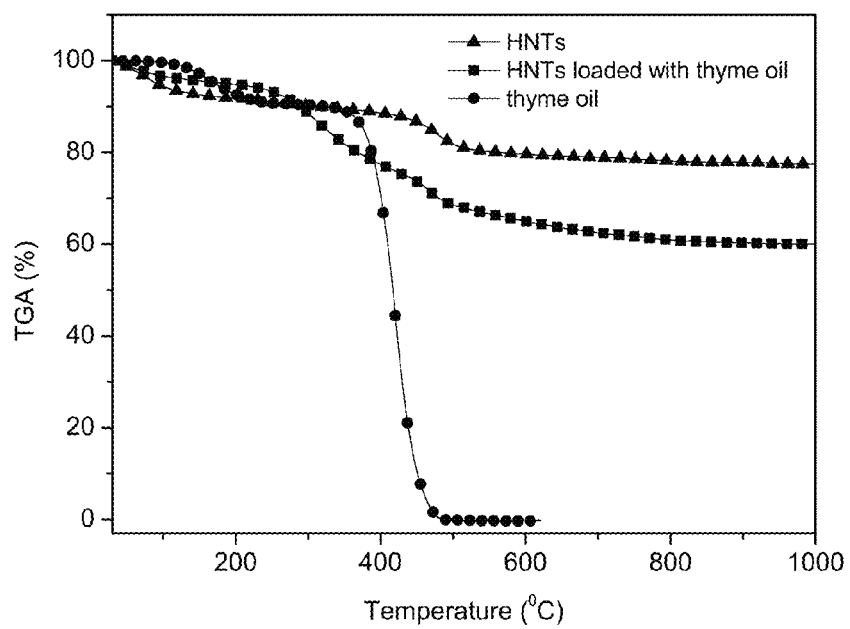
FIG. 2 shows a TGA analysis of empty HNTs, thyme oil alone, and thyme oil loaded HNTs according to the present invention.

The need for a system that enables controlled loading/release of natural antibacterial agents into/from the polymeric films is resolved in the present invention by using antibacterial agent loaded HNTs incorporated into said polymeric films. The inventors surprisingly found that essential oils and their active components in the sense of the present invention can well be incorporated into said nanotubes which results in a controlled release system for the antibacterial agents such that a more pronounced effect can thus be achieved in order to preserve the food material for a longer term. Antibacterial agents can be stored in HNTs such that they can be released in a controlled manner over the food sample covered by the polymeric film containing these HNTs. Hollow HNTs are efficient nano-containers that can be easily loaded with essential oils or their active components, for instance via a sonication and/or vacuum filling process. FIG. 2 shows a TGA analysis of empty HNTs, thyme oil alone, and thyme oil loaded HNTs, and it is thereby demonstrated that HNTs according to the current invention can be a useful ingredient in polymeric packaging films as nanocontainers of antibacterial agents.

The barrier properties of the disclosed packaging material can be obtained from the empty and/or antibacterial agent loaded HNTs that are dispersed throughout the polymeric film. HNTs dispersed in the polymeric film create a tortuous path for the gas molecules and prevent them from entering the food medium. The hydrophilic surface along with the high aspect ratio of HNTs makes HNTs effective fillings in polymeric nanocomposites for the prevention of gas permeation. Moreover, absorption of gases by the HNTs will contribute to the barrier property of the food packaging material. Thus, according to another aspect of the present invention, a polymeric food packaging material is provided with good barrier properties.

According to a further aspect of the present invention, there is provided a polymeric food packaging material exhibiting ethylene scavenging properties which advantageously extends the shelf life of the food product. The most common commercially used approach to remove ethylene gas has been using of potassium permanganate encapsulated in various carriers. While this is an effective method, the toxicity of potassium permanganate contradicts with the viability. As an alternative approach porous clay heterostructures have been incorporated into polymeric films for their ability to absorb ethylene gas. However, hollow nanotubular structures of clay have never been reported as a component of polymeric films for food packaging material with ethylene scavenging property. The inventors of the present invention noted that HNT containing polymeric films can serve as an excellent scavenger for ethylene, as well as O2, CO2, moisture and odors.

To this end, various aspects of the present invention provide HNT containing food packaging materials, wherein;

HNTs serve as nano-containers for essential oils and their active components having antibacterial activities, HNTs serve as ethylene gas scavengers, and HNTs serve as nano-fillers for food packaging material with barrier properties in addition to the functions above.

The essential oils to be loaded into HNTs as antibacterial agents can be chosen from thyme oil, oregano oil, cinnamon oil, lemongrass oil, peppermint oil, lavender oil, rosemary oil, coriander oil, clove oil and turmeric oil. Other antibacterial components to be loaded are the active components of essential oils and include thymol, carvacrol, cinnamic aldehyde, neral, geranial, menthol, eugenol, cineol, linalool.

HNTs in the sense of the present invention can be incorporated into the polymeric packaging material by way of the conventionally known methods such as solution or melt mixing or coated on the polymeric packaging material by way of known methods such as layer-by-layer thin film coating.

In an exemplary process, the said antibacterial agent is initially mixed with HNTs and ultrasonicated followed by application of vacuum to evacuate the air inside through channels of the HNTs and to fill the channels with the antibacterial agent. If HNTs are desired to be free of antibacterial agents, they can be directly used as they are. If antibacterial agents are used, the loaded HNTs are then centrifuged to remove the excessive antibacterial agent and subsequently dried to bring them into powder form. HNTs obtained in this way can directly be mixed with molten polymers or can be coated over the polymer film surface as mentioned above. In a mixing process, HNTs can be dispersed into the polymer matrix via a high speed melt mixer and a screw extruder and polymeric films are produced by known methods such as blown film or cast film processes. Alternatively a coating process can be implemented for application of the HNTs through surfaces of the polymeric film, in which case, HNTs are advantageously not deteriorated through high temperature effect of the simple mixture process mentioned above. This process enables a more rapid release rate of the active agent (i.e. antibacterial) and more effective scavenging properties because the HNTs are brought into close proximity with the food material inside the packaging. This method is also known as layer-by-layer (LbL) method where oppositely charged layers can be incorporated to each other via electrostatic principles on the surface of the polymeric food packaging film. In an exemplary method, HNTs can be loaded onto the charged surface of the polymeric film and this process can be repeated until the desired level of film thickness.

Figure 3:
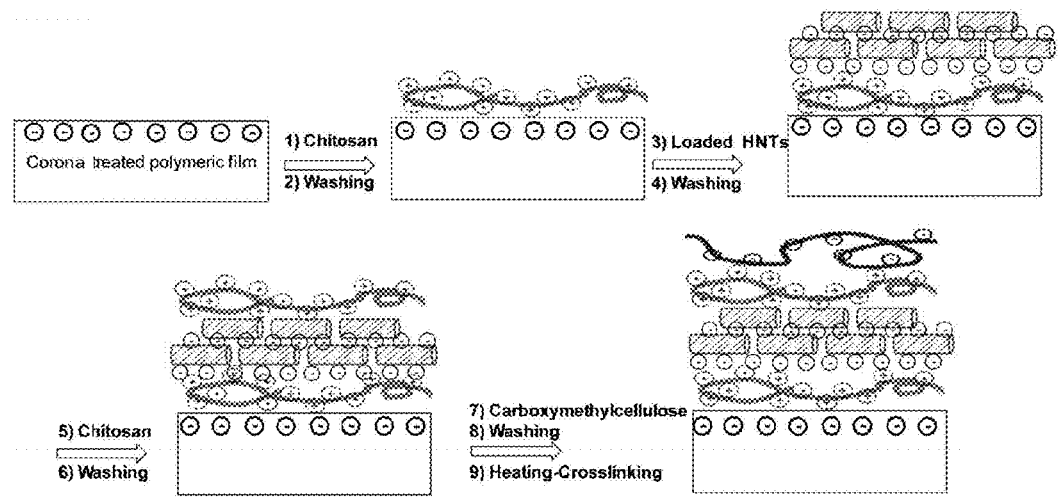
FIG. 3 shows an exemplary process for coating of halloysite nanotubes over the polymeric films according to the present invention.

According to preferred embodiments of the present invention chitosan as a natural polymer is used in a charged state, and is applied onto the charged surface of the polymeric film before adhesion with HNTs. Charged surface of the polymeric film can be achieved by well known oxidation treatments such as corona or plasma. An exemplary process is demonstrated in FIG. 3 which involves coating of HNTs onto chitosan coated charged polymeric films until desired number of bi-layers is achieved, which then can be further coated with chitosan and/or other natural charged polymers such as anionic carboxymethylcellulose (CMC). In this respect, the present invention enables an efficient process even with polymers of low surface energy such as PE and PP, and using of natural polymers complies with objectives of the current invention that is provision of natural and safer packaging materials. Chitosan is obtained through deacetylation of chitin, and is a natural, biodegradable polycarbohydrate that is approved as a reliable and safe material and is also recited as a material that can be used in eatable packaging materials in the literature. It has also antibacterial properties and the inventors noted that it prominently contributes to antibacterial effect of the essential oils stored in HNTs of the current invention.

The inventors noted that antibacterial, barrier and scavenging properties of the HNT containing polymeric films can be improved by further modifications as disclosed in the following embodiments.

The inventors noted ethylene scavenging properties of the HNTs can be considerably increased by increasing the surface area thereof, and treatment with H2SO4 is noted as a useful method to achieve this object. Hence according to another embodiment of the present invention, method of producing HNT loaded polymeric films further comprises treatment of HNTs with H2SO4. As a further method to eliminate the perishing effect of ethylene is realized by using 1-methylcyclopropen (1-MCP) which is an agent having binding affinity to ethylene receptors, and thereby inhibiting ethylene and its negative effects. The inventors found that 1-MCP can be successfully incorporated into some or all of the HNTs according to the present invention.

Figure 4:
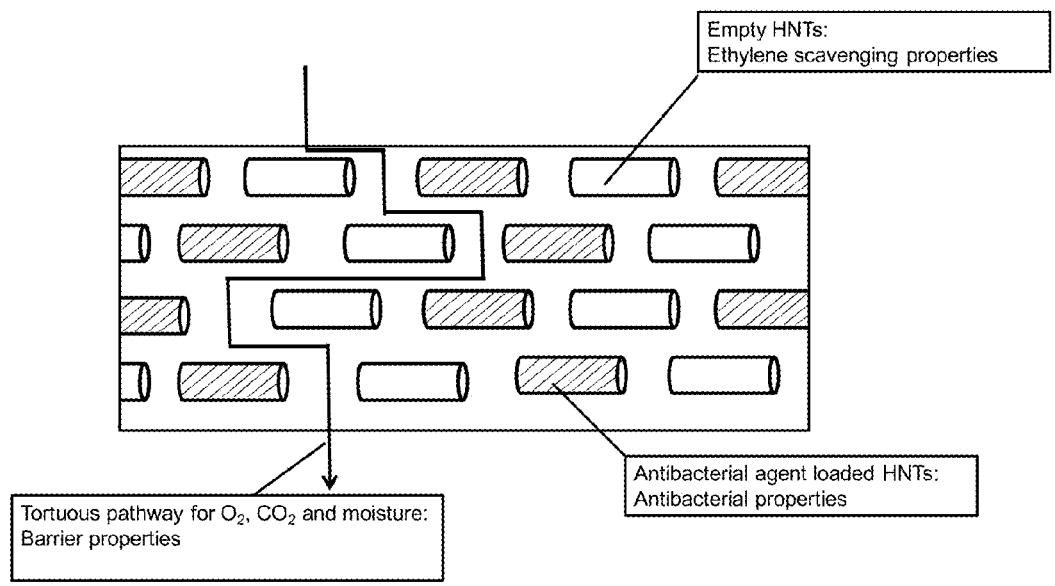
FIG. 4 shows distribution of loaded and empty halloysite nanotubes over a polymeric film according to an embodiment of the present invention.

According to further embodiments of the present invention, HNTs are provided as a mixture of empty and loaded ones. In this respect, the present invention provides two basic arrangements, in randomly mixed and layer by layer forms as shown in FIGS. 4 and 5, respectively.

As mentioned in the foregoing description, empty HNTs serve as ethylene scavengers while the loaded ones release antimicrobial agents in a controlled manner. The embodiment shown in FIG. 4 that is designed as a mixture of empty and loaded HNTs exhibits a tortuous pathway which advantageously improves barrier properties whereas the mixture in this form is suitable to release antibacterial agents with a comparatively slower rate and ethylene scavenging with a comparatively higher rate.

Figure 5:
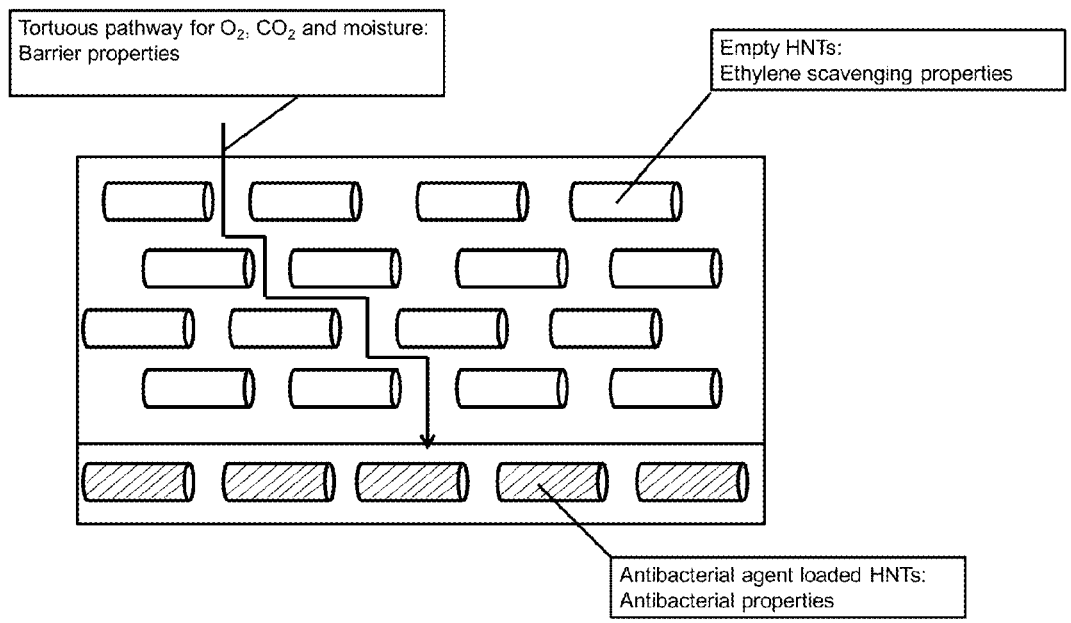
FIG. 5 shows a special arrangement of loaded and empty halloysite nanotubes according to another embodiment of the present invention.

In another embodiment as shown in FIG. 5, hollow HNTs are provided in a layer-by-layer arrangement with HNTs loaded with antimicrobial agents. In this embodiment said loaded HNTs are provided in close proximity with the food product which enables a comparatively higher release rate of the antibacterial agents. This embodiment is particularly advantageous because it can be prepared by way of an LbL method which is different than a melt mixing procedure which exerts excessive amount of heat to HNTs. This method eliminates the detrimental effect of the heat on antibacterial agents.

The present invention makes use of HNTs in polymeric packaging materials, preferably in thermoplastics and thermosettings for packaging purposes. The preferred polymers or films include polyethylene, polypropylene, polystyrene, polyurethane, polyvinyl chloride, polyester, fluoropolymers, poly(lactic acid), poly(caprolactone), polycarbonate, and polyamide or a copolymer, a mixture or a laminated film thereof.

We claim:

1. A method for producing a polymeric film for packaging of food products comprising incorporation of halloysite nanotubes into said polymeric film, wherein the halloysite nanotubes comprise a combination of empty nanotubes in the polymeric film and nanotubes loaded with an antibacterial agent the halloysite nanotubes being coated over the polymeric film, and wherein the nanotubes coated over the polymeric film are being arranged in close proximity on the food product side of the packaging film, and wherein the coating of the nanotubes loaded with an antibacterial agent comprises the steps of charging surface of the polymeric film;
    applying chitosan over the charged surface; and
    coating loaded nanotubes over chitosan layer.

2. The method according to claim 1 wherein the antibacterial agent is selected from the group consisting of natural essential oils and their active components.

3. The method according to claim 2 wherein the essential oil is selected from the group consisting of thyme oil, cinnamon oil, oregano oil, cinnamon oil, lemongrass oil, peppermint oil, lavender oil, rosemary oil, coriander oil, clove oil, turmeric oil, and active components thereof including carvacrol, thymol, cinnamic aldehyde, neral, geranial, menthol, eugenol, cineol and linalool.

4. The method according to claim 1 wherein the polymeric film is made of polyethylene or polypropylene.

5. The method according to claim 1 wherein the method comprises melt mixing of the halloysite nanotubes with the polymeric material.

6. The method according to claim 1 wherein the method further comprises a coating step for coating said loaded nanotube layer with halloysite nanotubes provided in an empty arrangement for scavenging purposes.

\* \* \* \* \*